United States Patent
Buehs (10) Patent No.: US 9,039,607 B2
(45) Date of Patent: May 26, 2015

(54) SHAFT ELEMENT FOR AN ENDOSCOPIC INSTRUMENT

(75) Inventor: Florian Buehs, Berlin (DE)

(73) Assignee: KARL STORZ GMBH & CO. KG (DE)

( * ) Notice: Subject to any disclaimer, the term of this patent is extended or adjusted under 35 U.S.C. 154(b) by 426 days.

(21) Appl. No.: 13/209,096

(22) Filed: Aug. 12, 2011

(65) Prior Publication Data

US 2012/0041266 A1    Feb. 16, 2012

(30) Foreign Application Priority Data

Aug. 13, 2010   (DE) .................. 10 2010 034 378

(51) Int. Cl.
*A61B 1/008* (2006.01)
*A61B 1/005* (2006.01)

(52) U.S. Cl.
CPC ............... *A61B 1/008* (2013.01); *A61B 1/0057* (2013.01)

(58) Field of Classification Search
CPC .. A61B 1/0051; A61B 1/0053; A61B 1/0055; A61B 1/0056; A61B 1/0057; A61B 1/008; A61B 2017/00323; A61M 26/0138; A61M 26/0147
USPC ........ 600/141, 142, 146; 604/95.04; 606/129, 606/130
See application file for complete search history.

(56) References Cited

U.S. PATENT DOCUMENTS

| | | | |
|---|---|---|---|
| 6,036,636 A | 3/2000 | Motoki et al. | |
| 6,780,151 B2 | 8/2004 | Grabover et al. | |
| 6,870,343 B2 * | 3/2005 | Borenstein et al. | 318/568.16 |
| 2003/0191367 A1 * | 10/2003 | Belson et al. | 600/146 |
| 2005/0131279 A1 | 6/2005 | Boulais et al. | |
| 2006/0070775 A1 * | 4/2006 | Anhalt et al. | 180/9.1 |
| 2008/0027285 A1 | 1/2008 | Yasunaga | |
| 2009/0171154 A1 | 7/2009 | Sutoh | |

FOREIGN PATENT DOCUMENTS

DE       29907430 U1     9/1999
DE   102007001580 A1     7/2007

OTHER PUBLICATIONS

German Search Report; Application No. DE 10 2010 034 378.1; Issued: Nov. 5, 2010; 3 pages.

* cited by examiner

*Primary Examiner* — Anhtuan T Nguyen
*Assistant Examiner* — Aaron B Fairchild
(74) *Attorney, Agent, or Firm* — St. Onge Steward Johnston & Reens LLC

(57) ABSTRACT

A shaft element for an endoscopic instrument includes a first, proximal shaft segment and a second, distal shaft segment, such that the second shaft segment is connected with the first shaft segment by three connecting elements, such that the connecting elements each include a first two-axis joint, such that the first joints form a triangle and such that the first connecting element is connected with the first shaft segment in such a way that it cannot slide with respect to the latter in a longitudinal direction, and a second and third connecting elements can each be slid with respect to the first shaft segment in a longitudinal direction independently of one another. The invention also relates to an endoscopic instrument, in particular an endoscope with such a shaft segment.

9 Claims, 5 Drawing Sheets

SHAFT ELEMENT FOR AN ENDOSCOPIC INSTRUMENT

CROSS-REFERENCE TO RELATED APPLICATIONS

The present application claims priority of German patent application No. 10 2010 034 378.1 filed on Aug. 13, 2010, the content of which is incorporated herein by reference.

FIELD OF THE INVENTION

The present invention relates to a shaft element for an endoscopic instrument, in particular for an endoscope with a bendable endoscope point.

BACKGROUND OF THE INVENTION

Endoscopes are used today for a number of applications in medicine and technology. Endoscopes typically include a rigid or flexible longitudinally extended shaft that is suitable for insertion into a cavity and on whose point an endoscope object lens is positioned to generate an image of a scene in the observed cavity. To record and retransmit the endoscopic image from the distal (that is, removed from the observer) end of the endoscope to the proximal end (close to the observer), it is possible for example to foresee an arranged bundle of light conductor fibers inside the shaft or an electronic image recorder, for example a CCD chip, in the area of the distal end of the shaft as well as electric lines inside the shaft. For rigid endoscopes, lens systems that can include a number of rod lenses can also be used to retransmit the image. Because sufficient light is usually not available as a rule in the observed cavity, a light conductor system is also foreseen inside the shaft in order to transport sufficient light to the distal end of the endoscope where it is used to illuminate the cavity.

In a number of applications it is desirable to be able to bend the distal end of the endoscope shaft, that is, the endoscope tip, to be able to modify not only the alignment of the endoscope tip but also the viewing angle of a lens positioned in the endoscope tip. Thus, for example in gastroscopy, sigmoidoscopy or bronchoscopy, use is made of endoscopes in which the shaft is configured to be flexible at least for a great part of its length and the endoscopic tip can be displaced to facilitate insertion of the endoscope into the cavity and to adjust the viewing angle to the particular requirements. For similar reasons, in the industrial field as well it is possible to use endoscopes with a long, flexible shaft, for example in investigating larger machinery with complex internal spaces such as turbines or combustion chambers.

In laparoscopy as well, a bendable endoscopic tip can be advantageous. Thus the restricted working area, as determined by the gas-filled abdomen in endoscopic operations, can be observed more comfortably with an endoscope whose tip is bendable. For this purpose, a short endoscopic tip, which can be bent at a large angle, is particularly advantageous. It can take the form, for example, of the tip of an endoscope with an otherwise rigid shaft.

To displace the bendable endoscope tip, it can be controlled by an operator, possibly along with other portions of the flexible endoscope shaft, from the proximal end of the endoscope.

To allow controllable bending of part of a flexible endoscope shaft, it is standard in the art to configure said shaft with a base structure made up of individual segments that can be pivoted with respect to one another. Thus, for example from DE 10 2007 001 580 A1, it is known that successive segments can be connected with one another by a single-axis pivot joint in each case and can be displaced at a small angle with respect to one another. According to U.S. Pat. No. 6,780,151 B2, a number of solid-state joints are aligned along the shaft. To displace the entire shaft or else the endoscope tip, tractive cables are provided that are fed through the endoscope as far as an actuating device located in the handle. Here every segment can be pivoted by a small angle with respect to the preceding or succeeding one. Bending by a large angle, for example 45 or 90 degrees, therefore requires a number of such segments and thus a relatively long endoscope tip, and thus it becomes impossible to use this endoscope in applications in which a small bending radius is necessary. In addition, in the bending process the individual segments mutually influence one another. If it is possible to bend only within a plane, then in order to be able to observe the entire space the shaft of the endoscope must be turned on its longitudinal axis; however, in the process the image recorded by the video camera turns correspondingly along with it, making orientation in the cavity difficult for the operator. If, on the other hand, a bending in several planes becomes possible by alternately rotated pivot axes by 90 degrees in each case, then this requires twice the number of segments, leading to a still greater minimum bending radius.

Patent US 2005/0131279 A1 discloses an endoscope shaft in which every segment allows a displacement around two axes that are perpendicular to one another, relative to the succeeding or preceding segment. Here too, however, the angle of displacement is relatively small, and therefore a small bend radius of the shaft or of the tip is not possible. According to US 2008/0027285 A1, segments of the shaft of an endoscope are connected together by several flexible connecting sections made up of spiral springs, such that the connecting sections can be bent in several planes with the help of cable pulls. Because of the flexibility of the connecting sections, however, an unintended displacement of the endoscope segments with respect to one another can occur. In addition, as a result of the tractive force there can be a change in length at an angle, impeding operating ability, along with an abrasion of the cable pulls.

U.S. Pat. No. 6,036,636 discloses an endoscope with a bendable tip, wherein the tip is connected with the endoscope shaft by a number of wires, so that bending of the tip can be accomplished by sliding the wires in relation to one another. The endoscope contains at least one elastic wire around which the endoscope tip can be bent, and at least one elastic pull or push wire with which the endoscope tip can be bent at an angle. Depending on the number of wires, the tip of the endoscope can be bent in all directions. In the process, because of the strong bending of the wires and the considerable pressure in bending, there is a danger of wearing out the material or breaking it, especially with large bending angles.

Patent US 2009/0171154 A1 discloses an endoscope whose distal end is bent by having an inner part of the endoscope extended with respect to the outer shaft, the outer shaft and the bendable tip being connected with one another by a strap. As a result, bending can occur only in one plane and in one direction.

According to patent DE 299 07 430 U1, a prism combination is positioned on the distal end of a rigid endoscope shaft, and in said prism combination the optical axis is deflected twice by 90 degrees each time. By means of a rotary mechanism the prisms are turned by 360 degrees to produce a desired viewing angle. In the process, however, complex mechanics are required for the displacement, and in addition the entire outer diameter of the shaft is increased, restricting the range of possible applications.

SUMMARY OF THE INVENTION

It is the object of the present invention to provide a shaft element for an endoscopic instrument that does not comprise the aforementioned disadvantages and that in particular allows a deflection in all spatial directions.

An endoscopic instrument of the aforementioned type comprises a shaft that is elongated in particular and is suitable for insertion into a cavity. The shaft can be of rigid or flexible configuration. In the context of the present application, an endoscopic instrument is understood to mean one that is suitable for insertion into a cavity and for observation inside the cavity and/or for performing manipulations inside the cavity, such that the possibility of optical observation is not an absolute necessity. Endoscopes for insertion into a cavity and for observation inside the cavity are among the endoscopic instruments as understood in this application.

A portion of the shaft of such an endoscopic instrument comprises, according to the invention, a number of segments, at least two of which can be tipped with respect to one another. As a result, for example, a bendable tip, which is connected with the distal one of the two segments that can be tipped with respect to one another, can be deflected with respect to the other shaft, which is connected with the proximal one of the two segments. Likewise, a distal portion of the shaft that is connected with a distal one of the two segments can be deflected with respect to a proximal portion of the shaft that is connected with the proximal one of the two segments. A shaft thus includes at least two segments that can be deflected with respect to one another and thereby form a shaft element for deflecting a tip or a portion of a shaft.

According to the invention a shaft element for an endoscopic instrument includes a first shaft segment positioned on the proximal end and a second shaft segment positioned on the distal end, which are connected with one another by three connecting elements. Said connecting elements each comprise a first two-axis joint, which allows tipping motions around two axes that are perpendicular to one another, which are each crosswise to a longitudinal axis of the shaft, in particular to a longitudinal axis of the second shaft segment. The first joints in particular are configured in such a way that they permit tipping in all directions but no rotation around a longitudinal axis of the connecting element or of the second shaft segment. The first three joints are positioned in the shape of a triangle, in particular in the form of a triangle standing crosswise to the longitudinal axis of the second shaft segment. The first three joints therefore not only lie on a straight line, thus determining an unequivocal position of the second shaft segment relative to the first shaft segment. In particular, the first three joints do not lie in a longitudinal plane of the second shaft segment or in a stretched position of the shaft element in the longitudinal plane of the shaft.

According to the invention, furthermore, a first of the three connecting elements is connected with the first shaft segment in such a way that the first connecting element cannot be slid in a longitudinal direction, in particular in a longitudinal direction of the first shaft segment, with respect to the first shaft segment. In particular, the first connecting element can be connected firmly or rigidly with the first shaft segment. A second and third of the three connecting elements can be slid independently of one another with respect to the first shaft segment in a longitudinal direction of the shaft, in particular in the longitudinal direction of the first shaft segment. By sliding the second and third of the connecting elements relative to the first shaft segment, and possibly the second and third connecting elements with respect to one another, a tipping of the second shaft segment relative to the first shaft segment is made possible in all spatial directions. The remaining portions of the shaft, which are connected with the first or second shaft segment, can be configured either rigidly or flexibly.

Because the second shaft segment is connected with the first shaft segment by three connecting elements, which each comprise a first two-axis joint, and because a first of the three connecting elements is firmly connected with the first shaft segment at least with respect to a longitudinal direction and a second and third of the three connecting elements can be slid with respect to the first shaft segment in a longitudinal direction of the shaft independently of one another, a diverting of the second shaft segment in simple manner becomes possible with respect to the first in all spatial directions without the connecting elements being impacted by strong bending motions that could lead to strain or fracturing of the material. Thereby a short tip can also be bent in all directions. In addition no rotation of the shaft is necessary in order to achieve all viewing angles. The recorded endoscopic image therefore remains intact.

According to a preferred embodiment of the invention, the first joints are positioned in the shape of an equilateral triangle that is crosswise to the longitudinal direction of the shaft or crosswise to a longitudinal axis of the second shaft segment. As a result, a control of the bending in all directions is achieved at a nearly constant transfer ratio between the sliding of the second and/or third connecting element and the achieved tipping angle, so that operation is simplified.

In a further advantageous manner, the first joints are positioned in or near a proximal end plane of the second shaft segment. The result is a compact and stable arrangement. In particular, a divertible tip of the endoscopic instrument can be configured as especially short, allowing use in narrow or flat cavities.

According to a particularly preferred embodiment, the second and third connecting elements each comprise a second two-axis joint. This second joint can be constructed in particular in similar manner as the first joint. Because the second and third connecting elements each comprise a second joint, an especially wear-resistant structure is achieved because the second and third connecting elements are not impacted by bending and therefore can be produced with rigid rods in the area of the shaft element, for example. The second joints as well are constructed especially to be rotation-resistant.

In an additional preferred embodiment of the invention, the second and third connecting elements are each configured as push rods that are rigid at least in some portions. In particular, the push rod can be rigid over its entire length, so that any bending of the push rod occurs only in the second joints. The push rod can also be configured as partly flexible in order to be able to follow the formation of the shaft in case of a flexible shaft. The push rod in particular is configured to transmit pushing and pulling motions and is therefore also referred to as a push rod. Because the connecting elements are each of rigid configuration at least in portions, an especially abrasion-free execution becomes possible.

It is further preferred that the second and third connecting elements or the push rods that constitute the second and third connecting elements, based on a cross-section of the first segment, are positioned in its peripheral area. As a result, on the one hand an especially large lever arm is produced for the bending of the second segment, while on the other hand there remains within the first segment an especially large free space for conducting cables, light conductors or other channels that must be fed from the proximal to the distal end of the endoscopic instrument or vice versa.

According to another embodiment, the first connecting element attaches in a peripheral area of the second segment, in particular in a peripheral area of a proximal end plane of the second segment. This has the advantage of an especially large lever arm for the bending and a large residual free space in the inner area of the second segment, especially when the second and third connecting elements likewise attach in a peripheral area, for example in the opposite peripheral area.

According to another embodiment, the first connecting element attaches centrally, in particular in the center of a proximal end surface, on the second segment. This has as a result that a bending of the second segment with respect to the first segment becomes possible in symmetrical manner in all directions.

Here, in especially advantageous manner, in the peripheral area of the first segment, especially in the peripheral area in which the second and third connecting elements or the corresponding push rods are fed through the first segment, the first connecting element can attach at this first segment. Consequently, in addition, a large area can be made available for passing lines through the first segment.

The first connecting element can, for example, have the form of an angled sidearm, which secures the position of the first joint of the first connecting element with respect to the first segment. In this embodiment the constructive area inside the first segment is restricted by the connecting elements to the least extent possible.

The two-axis joints can be configured in particular as cardan joints with two axes standing perpendicular to one another that, with the shaft element in extended position, are aligned perpendicularly to the longitudinal direction of the shaft. A cardan joint of this kind has the advantage of simple structure and great rigidity to rotary movements around the longitudinal axis.

The joints can also be made up of a spiral spring, a parcel of disc springs, an elastomer joint or a combination of solid-state joints. In addition the joints can be made with the help of a bellows, which can be constructed of metal or plastic. These solutions have the advantage of simple structure that can be miniaturized.

The push rods can be powered by manual actuation from the proximal end of the endoscopic instrument in a manner that is known in its own right. According to a preferred embodiment, powering occurs by actuators that are positioned inside the first segment or inside the shaft. Such actuators can, for example, be produced electromechanically, possibly with linear coil replacement, hydraulically or else pneumatically. Linear drives, artificial muscles or piezo linear drives are possible. The same types of drives can be produced on the proximal end, for example inside a handle, such that the transmission can occur by way of push rods to the shaft element.

The angling motion can be powered in particular by two simple engines. By determining one engine position, it becomes possible to draw an unequivocal conclusion concerning the position of the second segment and possibly thereby the position of the tip. In applications with virtual reality, augmented reality or integrated navigation, this information can be used, for example, to indicate the bending angle in an endoscopic image. In addition, a motion control of the tip of the endoscopic instrument configured as an endoscope can hereby be simplified, for example, by voice control or eye tracking.

To protect the lines and/or the angling mechanics against soiling, damage and the penetration of steam in autoclaving, a sheath can be provided, for example a bellows made of metal or of a high-performance plastic like PTFE. The movable components or the shaft element can also be surrounded with a protective layer or an elastomer sleeve.

An inventive endoscopic instrument includes a shaft with a bendable tip as well as a proximal operating part with operating elements and electric junctions, light junctions and/or other junctions. The shaft includes at least an inventive shaft element; in particular, a tip can be bendably connected by the shaft element with the other area of the shaft, which can be of rigid or flexible configuration. In preferred manner, an endoscope object lens and an electronic image recorder, for example a CCD chip ("chip on the tip"), are positioned inside the endoscope tip as well as possibly the light outlets of an illuminating lens. The supply and data lines of the electronic image recorder as well as the light conductors of the illuminating lens are fed through the shaft to the proximal end. The endoscope tip can also include a light source, possibly a light-emitting diode (LED) whose supply and possibly cooler lines run through the shaft. Likewise channels for feeding endoscopic instruments and/or irrigating or suction channels can be fed through the shaft.

In advantageous manner, in an endoscopic instrument several inventive shaft elements can be arranged one after the other. Here, the second shaft segment of a first shaft element in each case constitutes the first segment of a second shaft element or is connected with it. As a result, a greater bending angle and/or a multiple angling of the shaft becomes possible. In the process, for each bendable segment two actuators can be foreseen that can be positioned, for instance, in the respective first segments in the shaft. Consequently the individual anglings are combined with one another without influencing one another.

It is understood that the aforementioned characteristics, and those to be explained hereinafter, can be applied not only in the combination indicated in each case but also in other combinations or else individually, without departing from the framework of the present invention.

Further aspects of the invention can be seen from the following description of a preferred embodiment and from the appended drawings, which are as follows.

DETAILED DESCRIPTION OF THE INVENTION

Figure 1:
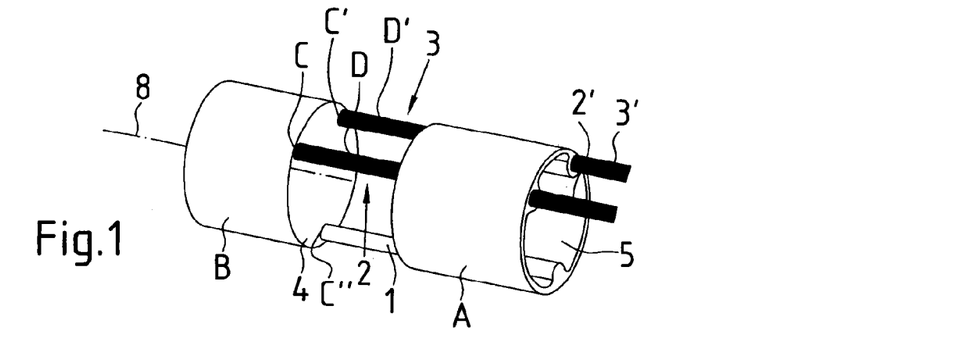
FIG. 1 shows a simplified depiction of the structure of an embodiment of the invention.

As shown in FIG. 1, a shaft element according to a first embodiment of the invention comprises two segments A, B, namely a proximal segment A and a distal segment B, which can be displaced, that is, bent at an angle, with respect to the first segment A. Between the two segments are situated three connecting elements 1, 2, 3. Said connecting elements 1, 2, 3 each comprise a joint C, C', C" at the point of connection to segment B. Said joints are constructed in such a way as to permit tipping in all directions but do not permit a rotation around an axis parallel to the longitudinal axis 8 of the second segment B or around the longitudinal axis of the shaft that coincides with the longitudinal axis 8 of the second segment B in the elongated position shown in FIG. 1. A first connecting element 1 is fixed in the segment A.

Two additional connecting elements 2, 3 are constructed as push rods 2', 3' or each is connected with a push rod 2', 3', so that the push rods 2', 3' are slidably mounted inside segment A and are fed through the first segment A in the proximal direction for actuation. The two connecting elements 2, 3 each comprise an additional two-axis joint D, D'. These joints too allow tipping in all directions, but permit no rotation around an axis parallel to the axis of the particular push rod. As shown in FIG. 1, the two push rods 2', 3' are fed through the peripheral area of segment A in order to allow as much space as possible for lines fed inside segment A, for example electrical supply and data lines or light conductors. According to the embodiment shown in FIG. 1, the first connecting element 1 is likewise positioned in the peripheral area of segments A, B.

The supporting points of the connecting elements 1, 2, 3 on the second segment B or the joints C, C' C" form an approximately equilateral triangle whose surface stands perpendicular on the longitudinal axis 8 of the second segment B and defines a proximal end plane 4 of the second segment B. The first segment A comprises a lumen 5 for feeding the electrical lines, lighting lines and/or additional channels that are not seen in FIG. 1. The second segment B also comprises a hollow space of this type (not illustrated).

Figure 2:
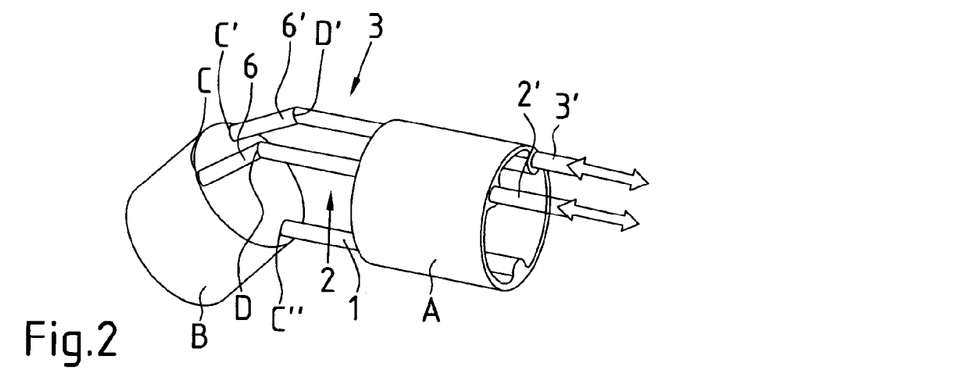
FIG. 2 shows the embodiment from FIG. 1 in a first angled position.
Figure 3:
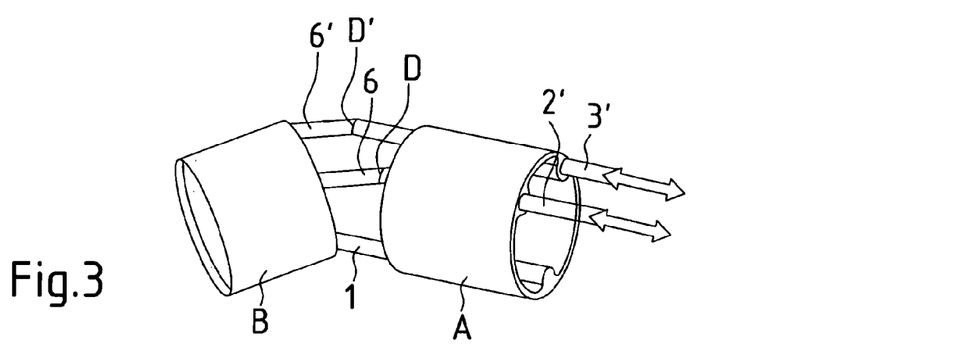
FIG. 3 shows the embodiment from FIG. 1 in a second angled position.

According to FIG. 2, the bending of segment B with respect to segment A occurs by a linear sliding of one or both push rods 2', 3' in the direction of the arrows. By extending or shortening the connecting elements 2, 3 or the part of the push rods 2', 3' found between the two segments, the joints C, C', C", D, D' are bent in defined manner and thereby a diagonal position of segment B is produced in relation to segment A. In the process, the connecting elements 2, 3 can each be configured as a rigid rod 6, 6' in their distal portion positioned beyond the joint D, D'. The direction and size of the angling of segment B are determined by the sliding of the push rods 2', 3'. If the displacement of the push rods 2', 3' is measured, then conclusions can be drawn about the actual bending and thus about the viewing angle of a tip connected with segment B. This can be used, for example, for virtual reality applications.

According to FIG. 1, the bending motion of the second segment always occurs around the joint C", that is, not symmetrically to the center longitudinal axis 8' of the first segment. A symmetrical bending motion can be achieved through a modification according to FIGS. 4a and 4b. Here the fixed connecting element 1 is configured as a doubly bent or angled sidearm 9 of the first segment A that attaches in the area between the push rods 2', 3' on the first segment A. The connecting point of the first connecting element 1 on the second segment B, that is, the joint C", on the other hand, is positioned centrally in the proximal end plane 4 of the second segment B.

Figure 4A:
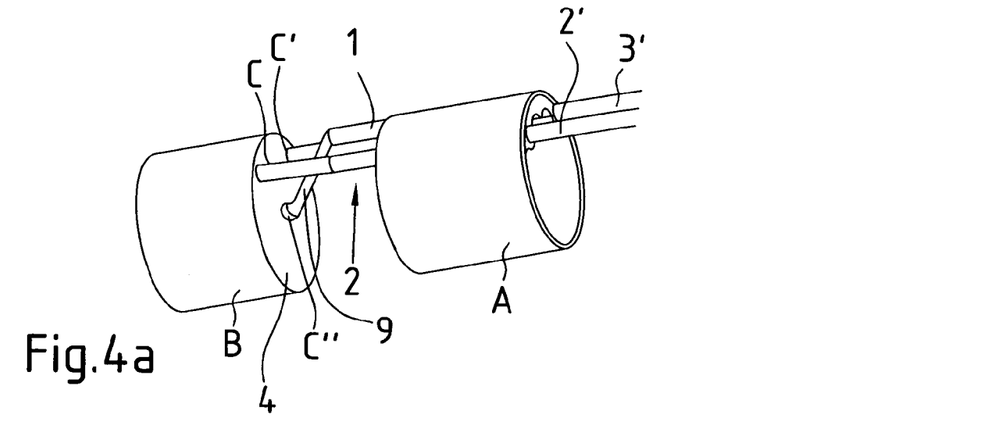
FIGS. 4a and 4b show a second embodiment of the invention in a schematic depiction in elongated or angled position.
Figure 4B:
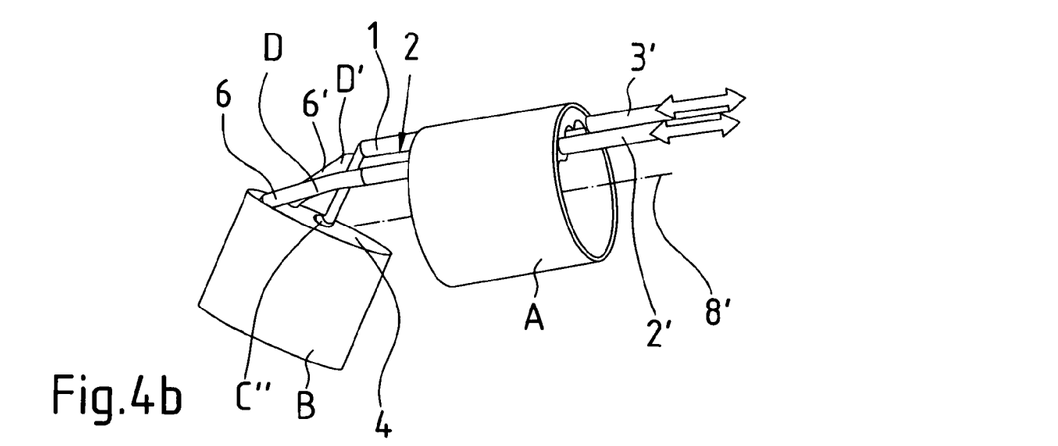

FIG. 4b shows an angled position of the embodiment from FIG. 4a. As can be seen in FIG. 4b, by sliding the push rods 2', 3' in the direction of the arrows, it is possible to control an angling of the second segment B in relation to the first segment A around a rotation point that lies on a center longitudinal axis 8' of the first segment A.

Figure 5A:
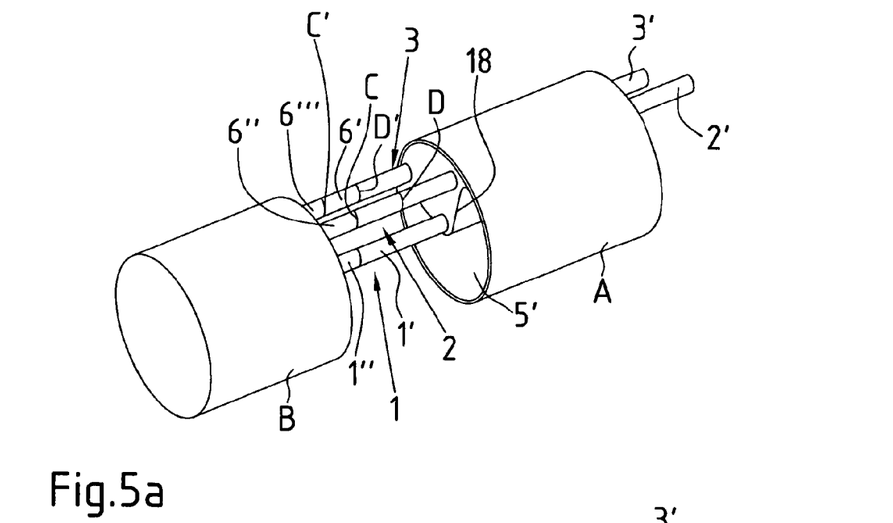
FIGS. 5a and 5b show a third embodiment of the invention in a schematic depiction in elongated or angled position.
Figure 5B:
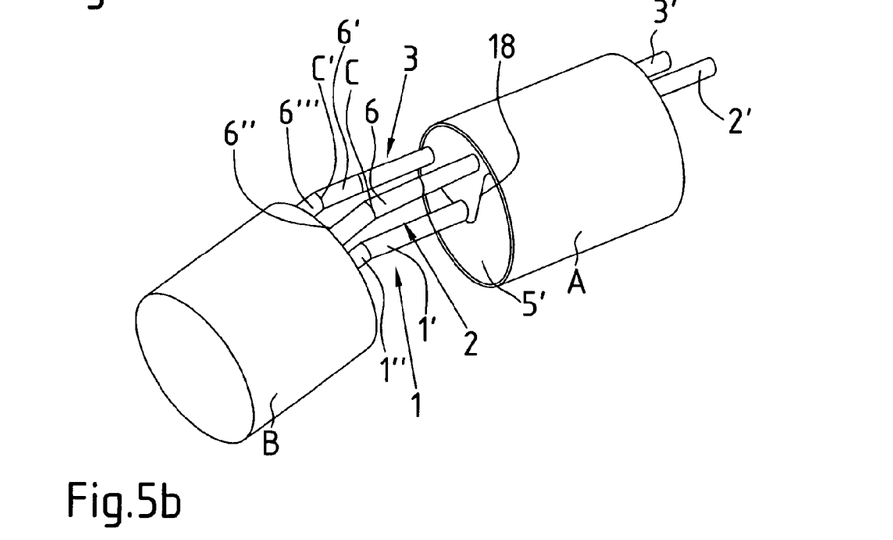

An additional embodiment of the invention is illustrated in FIGS. 5a and 5b. The joints C", C, C' of the connecting elements 1, 2, 3 in this embodiment form a triangle, which however is displaced in the proximal direction opposite a proximal end plane of the second shaft element B. For this purpose, the first connecting element 1 is configured as a partly rigid rod, such that a proximal portion 1' is connected rigidly with the first shaft segment A and a distal portion 1" is connected rigidly with the second shat segment B. The proximal portion 1' is connected with the distal portion 1" by the joint C". The second and third connecting elements 2, 3 are only each configured as a rigid rod 6, 6' in their portion positioned distally from the other joint D, D', but they also comprise an additional distal portion that is configured as a rigid rod 6", 6'" and is connected with the rod 6, 6' by the joint C, C'. The aforementioned distal portions of the second and third connecting elements 2, 3 are each rigidly connected with the second shaft segment B. In particular, the second and third connecting elements can each be configured as a jointed rod with two two-axis joints.

FIG. 5b shows an angled position of the embodiment from FIG. 5a. As is indicated symbolically in FIG. 5b by a shortening of the portions of the push rods 2', 3' extending proximally out of the proximal shaft element A, it is possible by sliding the push rods 2', 3' to angle the distal shaft segment B around a rotation point that is determined by the joint C'" of the first connecting element 1.

As can further be seen in FIGS. 5a and 5b, the first connecting element can attach at a protrusion 18 that is connected internally with a mantle of the first shaft segment A. Consequently, despite the restriction by the nearly centrally attaching first connecting element 1, there remains a relatively large lumen 5' for inserting additional functional elements of the endoscopic instrument.

Several of the described shaft elements can be positioned behind one another in an endoscopic instrument. In the process, for example, the proximal end surface of a first segment A can be configured to correspond with the proximal end surface 4 of the second segment B, on which connecting elements to an additional proximal segment attach (not illustrated). Owing to the sequential arrangement of several segments of the described type, or of several shaft elements, an especially flexible structure of a shaft can be achieved.

Rather than by push rods 2', 3' passed through the proximal segment A, the connecting elements 2, 3 can also be actuated by actuators that are positioned inside the proximal segment A. These actuators are controlled from the proximal end of the endoscopic instrument by operating elements and by control lines positioned inside the shaft. In this case as well, a precise positioning of the individual elements is possible.

The elements employed in an inventive shaft element should be as produced so that they are as small and free from friction and wear as possible. Excessively large joints would restrict structural space for other lines. Various possibilities for producing the joints C, C', C", D, D' are illustrated by way of example in FIGS. 6a through 6c and FIGS. 7a through 7d. In each case here, the joints D, D' are illustrated as a connection between rigid rods 7, 7', which are portions of the connecting elements; in similar manner, the joints C, C', C" can attach directly on the second shaft segment B or on a proximal end surface 4 of the second shaft segment B.

Figure 6A:
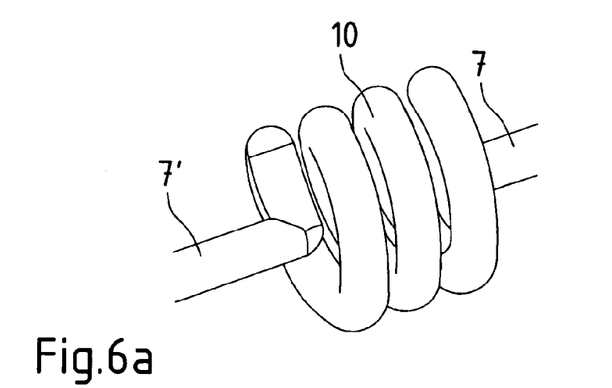
FIGS. 6a through 6c show various embodiments of a two-axis joint for use in an inventive shaft element.
Figure 6B:
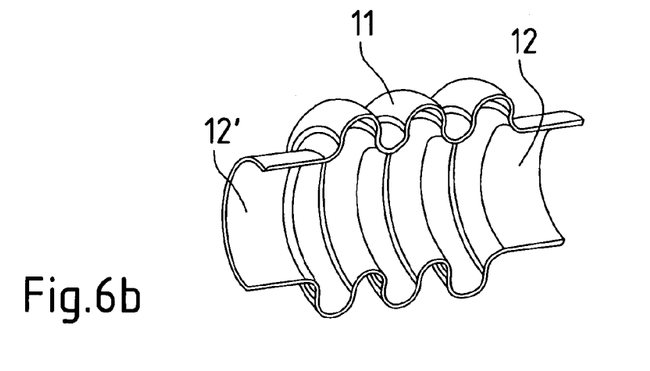
Figure 6C:
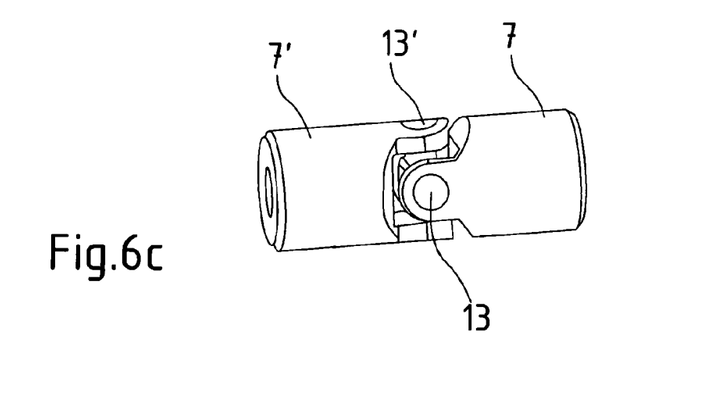

According to FIG. 6a, a very simple structure for a joint can be realized in the form of a spiral spring 10; likewise, for example, disc springs can be used. The springs can be produced, for example, of polymer or metallic materials. Another especially simple structure can result from a bellows 11 in whose end-surface apertures 12, 12' the ends of the rods 7, 7' can be firmly inserted (FIG. 6b). According to FIG. 6c, the joints can also be configured as miniature shaft couplings or cardan joints with two axes standing perpendicular to one another that can be realized by rods 13, 13' mounted rotatably. The joints can also be realized by solid-state joints.

Figures 7A, 7B:
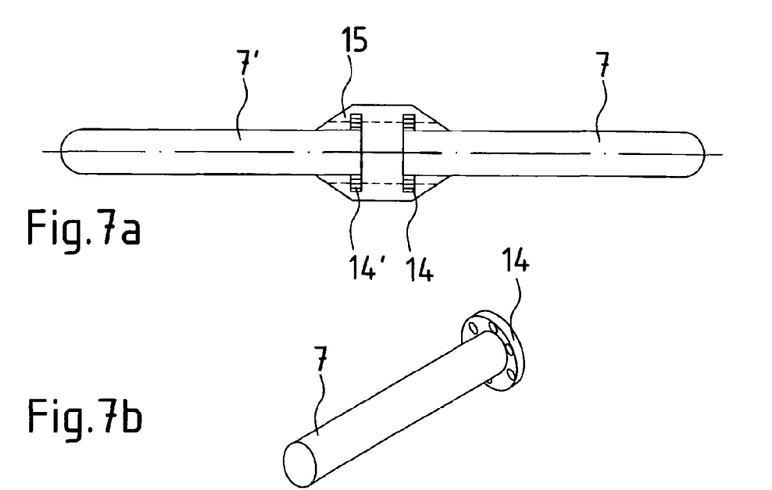
FIGS. 7a through 7d show additional embodiments of a two-axis joint for use in an inventive shaft element.
Figure 7C:
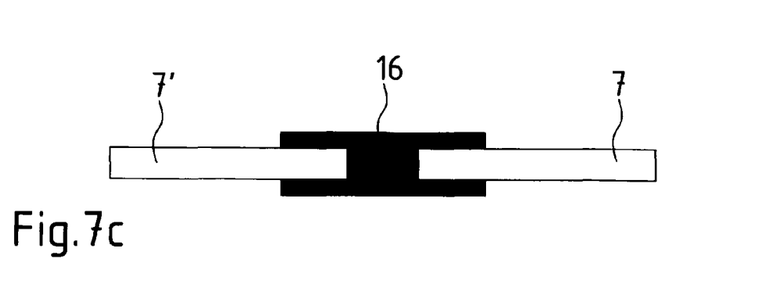
Figure 7D:
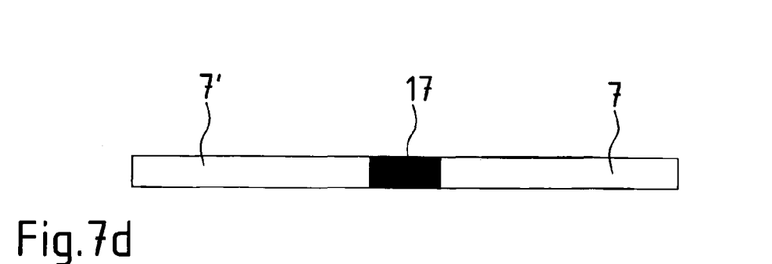

An additional possibility for configuring the joints is obtained from the use of elastomer materials. According to FIG. 7*a*, the ends of the rods 7, 7' are of flat configuration and are molded with an elastomer material. According to FIG. 7*b*, the plates 14, 14' can be equipped with boreholes in order to avoid rotation of the two parts with respect to one another. An even simpler structure can be achieved by a shrinkable or cementable elastomer, for example a hose 16 that, according to FIG. 7*c*, connects the two rods 7, 7' with one another. Likewise the rods 7, 7' can be connected together by an elastic intermediate piece 17 (FIG. 7*d*).

For the sake of clarity, all reference numbers are not indicated in all drawings. Given reference numbers retain the same significance in the illustrations.

What is claimed is:

1. A shaft element for a medical endoscopic instrument, the shaft element comprising:
    a first, proximal shaft segment; and
    a second, distal shaft segment, the second shaft segment being connected with the first shaft segment by three connecting elements;
    the connecting elements each having a first two-axis joint, the first joints being positioned from each other on a proximal end plane of the second shaft segment in a triangular shape, the first joints forming vertices of the triangular shape, the triangular shape being an equilateral triangle;
    wherein a first connecting element of the connecting elements is connected with the first shaft segment in such a way that the first connecting element is non-slidable with respect to the first shaft segment in a longitudinal direction, and a second and third connecting elements are each slidable in a longitudinal direction with respect to the first shaft segment independently of one another;
    wherein the second and third connecting elements are configured as at least partly rigid push rods.

2. The shaft element according to claim 1, wherein the second and third connecting elements each comprise a second two-axis joint.

3. The shaft element according to claim 1, wherein the second and third connecting elements attach in a peripheral area of the first shaft segment.

4. The shaft element according to claim 1, wherein the first connecting element attaches in a peripheral area of the second shaft segment.

5. The shaft element according to claim 1, wherein the first connecting element attaches centrally on the second shaft segment.

6. The shaft element according to claim 1, wherein one or more of the two-axis joints are configured as spring joint, elastomer joint, solid-state joint, bellows joint or cardan joint.

7. The shaft element according to claim 1, wherein one or more actuators associated with the first shaft segment slide the second and third connecting elements.

8. An endoscopic instrument with a shaft and operating part, wherein the shaft includes a shaft element according to claim 1.

9. The endoscopic instrument according to claim 8, wherein the shaft includes a plurality of shaft elements arranged one after another.

* * * * *